(12) United States Patent
Mitchell

(10) Patent No.: US 8,127,612 B2
(45) Date of Patent: Mar. 6, 2012

(54) SYSTEM AND METHOD FOR ULTRASONIC EXAMINATION OF THREADED SURFACES

(75) Inventor: James R. Mitchell, Mystic, CT (US)

(73) Assignee: Praxair Technology, Inc., Danbury, CT (US)

( * ) Notice: Subject to any disclaimer, the term of this patent is extended or adjusted under 35 U.S.C. 154(b) by 863 days.

(21) Appl. No.: 12/197,444

(22) Filed: Aug. 25, 2008

(65) Prior Publication Data

US 2010/0043559 A1    Feb. 25, 2010

(51) Int. Cl.
*A61B 5/04* (2006.01)
(52) U.S. Cl. .......................................................... 73/623
(58) Field of Classification Search ............... 73/618, 73/620, 622–623
See application file for complete search history.

(56) References Cited

U.S. PATENT DOCUMENTS

| | | | | |
|---|---|---|---|---|
| 3,703,037 A | * | 11/1972 | Robinson | 433/86 |
| 4,751,420 A | * | 6/1988 | Gebhardt et al. | 310/327 |
| 4,783,997 A | * | 11/1988 | Lynnworth | 73/644 |
| 5,025,215 A | * | 6/1991 | Pirl | 324/220 |
| 5,426,980 A | * | 6/1995 | Smith | 73/644 |

OTHER PUBLICATIONS

U.S. Department of Transportation, Pipeline and Hazardous Materials Safety Administration, DOT-SP 10922, Jan. 2008.
U.S. Department of Transportation, Pipeline and Hazardous Materials Safety Administration, DOT-SP 9847, Nov. 2008.

* cited by examiner

*Primary Examiner* — Max Noori
(74) *Attorney, Agent, or Firm* — Robert J. Hampsch

(57) ABSTRACT

A system and method for ultrasonic examination of a threaded test object, and more particularly, the mounting threads of a compressed gas tube while the tube is affixed to a tube trailer is provided. The disclosed ultrasonic test instrument includes a probe having one or more transducers for transmission and reception of ultrasound pulses, a contoured wear plate, and a shoe of highly attenuative material having a thread-like exterior surface adapted to mate with the threaded surface of the test object. The shoe further includes a narrow window in the thread-like exterior surface such that the shoe absorbs most of the ultrasonic pulses transmitted from the piezoelectric crystal except for the ultrasonic transmissions passing through the narrow window to the test object.

14 Claims, 3 Drawing Sheets

SYSTEM AND METHOD FOR ULTRASONIC EXAMINATION OF THREADED SURFACES

FIELD OF THE INVENTION

The present invention relates to ultrasonic examination of threaded surfaces, and more particularly to in-situ ultrasonic examination or inspection of mounting threads of a tube while the tube is affixed to a tube trailer.

BACKGROUND

The United States Department of Transportation requires periodic inspection of tube mounting threads on tube trailers used to transport compressed gases. In accordance with the current inspection procedure, to prevent the wear on the mounting threads of a tube from weakening the threaded connection to a point where safety may be compromised, the mounting threads on the tube must be inspected once every 10 years. The required inspection is a visual inspection using a Thread Pitch Gauge for measurement of the thread wear. Such visual inspection, however, requires removal of the mounting flanges. When evaluating the mounting threads on tubes, there are two basic categories of thread degradation that should be considered: generalized thread wear and isolated thread loss. Generalized thread wear is the erosion of the mounting threads over a significant area due to the relative motion between the tube and the mounting flange and is characterized by a measurably shorter height of the threads in the area engaged by the mounting flange.

Current examination and inspection methods require the actual removal of the tube from the trailer chassis to a dedicated test bench or inspection station. Removing the tube from the trailer chassis for examination and inspection typically involves the use of a crane to remove the tubes from the trailer chassis and the use of cutting torches to remove the mounting flanges from each end of the tubes. Once the tubes are removed from the trailer chassis, the tube is moved to a test station and the mounting threads on each end of the tubes are visually inspected and thread measurements are taken. Such current methods are labor intensive and generally expensive procedures.

In an effort to improve the quality and automate the inspection process, ultrasonic examination systems have been proposed. An example of an ultrasonic cylinder examination system is the system offered by FIBA Technologies, Inc. of Millbury, Mass. The FIBA Technologies ultrasonic cylinder examination system includes an array of ultrasonic transducers mounted in a customized probe. The gas cylinder is brought to a test station or test trailer where it is rotated and the ultrasonic wall thickness measurements are taken at specific intervals in a helix pattern. The FIBA system allows re-qualification of compressed gas cylinders without having to remove the valve or remove the product. However, removal of the gas cylinder from the tube trailer and removal of the mounting is still required. Moreover, The FIBA Technologies ultrasonic cylinder examination system is designed to inspect the cylindrical and shoulder sections of the gas cylinder. It is not capable of examining the end or mounting threads.

AE/UT recertification of tubes is recognized by the United States Department of Transportation. This technique does not require removal of the tubes from the trailer. What is needed is a lower cost system and method for ultrasonic examination of the mounting threads that does not involve the removal of the tube from the tube trailer.

SUMMARY OF THE INVENTION

In one aspect, the present invention may be characterized as a method for ultrasonic inspection of mounting threads on a tube while the tube is affixed to a tube trailer. The method generally comprises the steps of (i) removing a tube valve and an end plug from an end of the tube which defines an opening on the tube exposing an interior surface, which is typically threaded; (ii) inserting the probe into the opening and in contact with the exposed interior surface; (iii) directing test signals from the probe towards the exterior threaded surface and receiving reflected signals therefrom; and (iv) analyzing the reflected signals to ascertain thread conditions on the exterior threaded surface.

In another aspect, the present invention may be characterized as an ultrasonic test instrument for examining threaded test objects or examination articles. The present ultrasonic test instrument comprises: a probe having one or more transducers with a piezoelectric crystal for transmission and reception of ultrasonic signals; a wear plate disposed adjacent to the ultrasonic transducer(s) and piezoelectric crystal to protect the ultrasonic transducer(s) piezoelectric crystal from abrasion; and a shoe disposed around the probe and wear plate. Particular features of the present ultrasonic test instrument include a thread-like exterior surface on the shoe adapted to mate with the threaded surface of the test object or examination article. The probe further includes a narrow window in the thread-like exterior surface of the shoe wherein the shoe absorbs the ultrasonic pulse energy transmitted from the transducer(s) except for the energy passing through the narrow window. Another useful feature of the present probe is that the wear plate is preferably contoured in the shape of a lens to focus the energy and localize the contact between the wear plate and the peak of the thread through which the ultrasonic waves will pass into the examination article. Such localized contact improves the alignment of the probe with the examination article and optimizes the signals used during the test procedures.

BRIEF DESCRIPTION OF THE DRAWINGS

The above and other aspects, features, and advantages of the present invention will be more apparent from the following, more descriptive description thereof, presented in conjunction with the following drawings, wherein.

DETAILED DESCRIPTION

Figure 1:
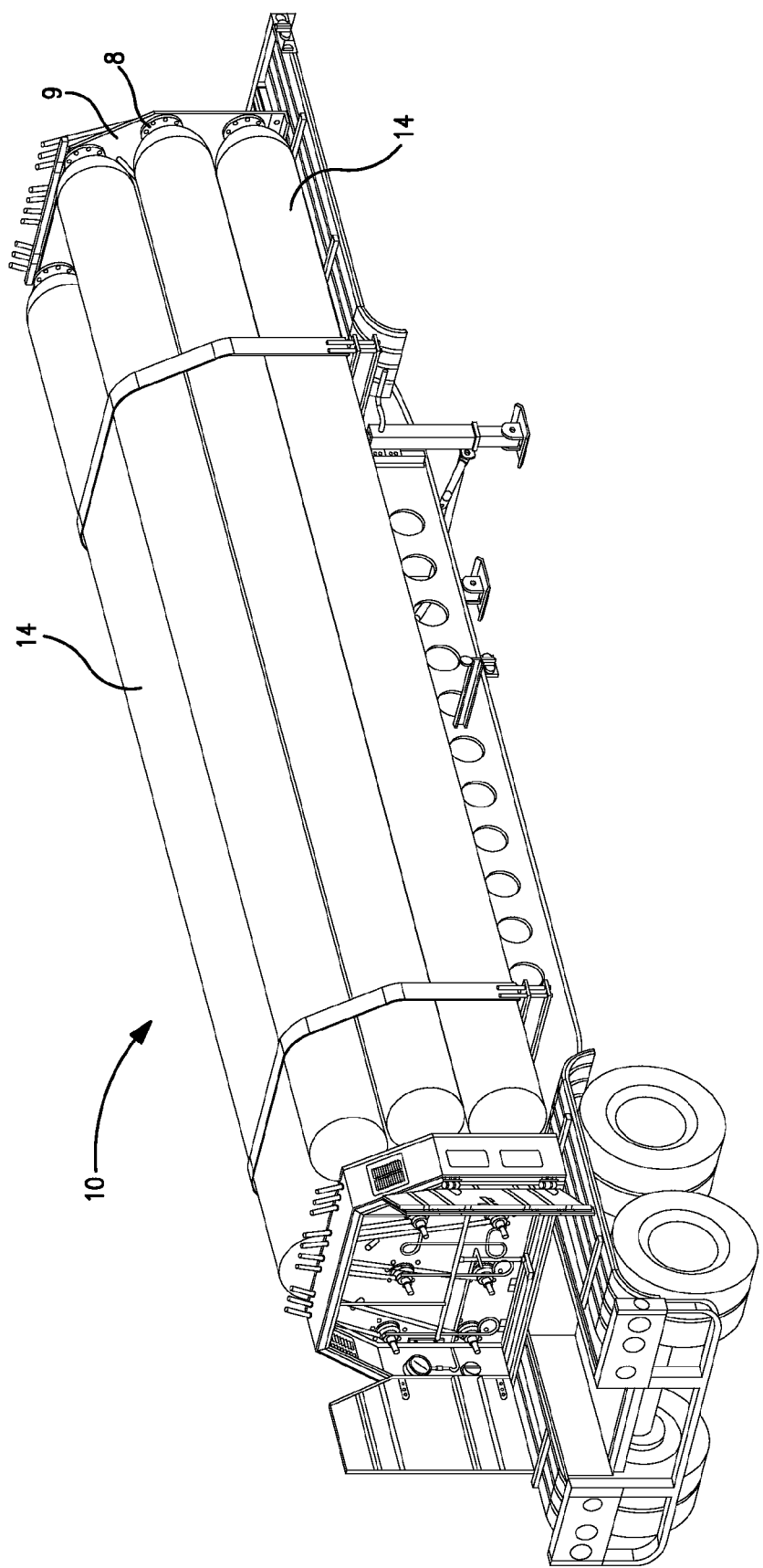
FIG. 1 depicts an illustration of a tube trailer.
Figure 2A:
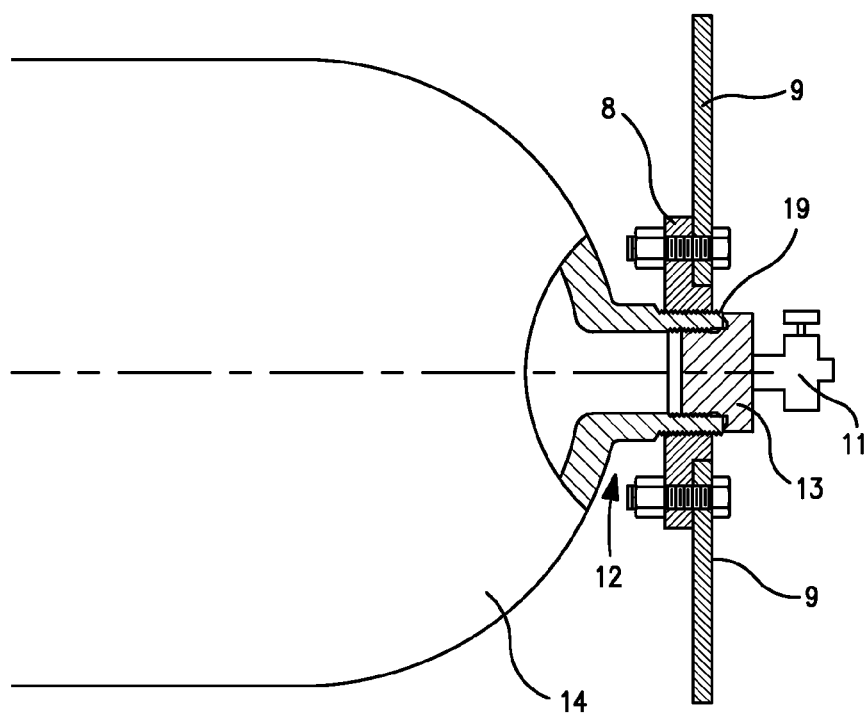
FIG. 2A depicts a partial cross section view of a tube mounted on a tube trailer.
Figure 2B:
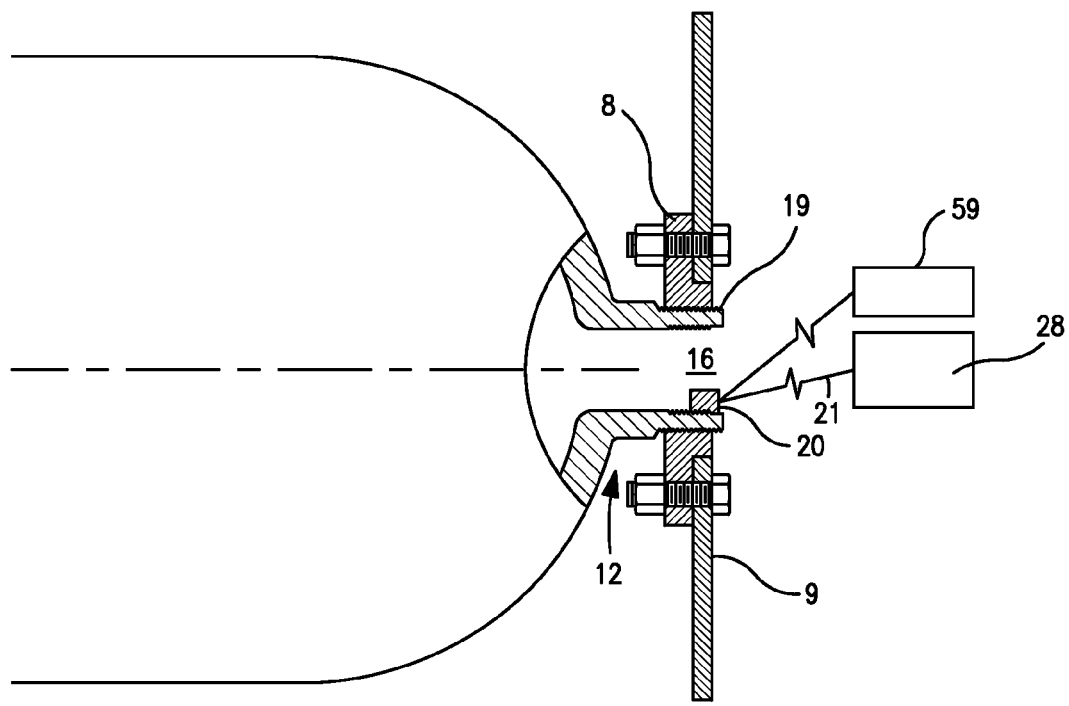
FIG. 2B depicts a partial cross section view of a tube mounted on a tube trailer with the probe disposed in the neck of the tube and used to examine a threaded surface of the tube.

Turning now to the Figures, there are shown illustrations of a tube trailer together with the present probe for ultrasonic examination of mounting threads. More particularly, FIGS. 1 through 3 present illustrations of the typical structural arrangement of compressed gas cylinder tube trailers as well as the probe as it is used during examination of the mounting threads of the type typically found on such compressed gas cylinder tube trailers.

Utilizing the illustrated embodiment of the probe 20, the preferred method for inspecting mounting threads 19 on a tube 14 affixed via a mounting flange 8 to a bulkhead 9 of tube trailer 10 is accomplished without removing the tube from the tube trailer 10. The preferred method involves first removing the tube valve 11 and an end plug 13 from an end or neck 12 of the tube 14 to define an opening 16 on the neck 12 exposing an interior surface 17. The next step involves inserting the probe 20 into the opening 16 and placing it in direct contact with the exposed interior surface 17 of the neck 12. The probe 20 is subsequently activated such that ultrasonic test signals 40 are launched from the piezoelectric crystal 24 of the ultrasonic transducer 22. Some of the ultrasonic test signals 40 reach the interior surface 17 and propagate through the neck 12 of the tube 14 to the mounting threads 19 where the test signals are reflected back towards the ultrasonic transducer. The reflected test signals 42A, 42B are received by the ultrasonic transducer 22, converted to electrical signals 21 and subsequently analyzed in the ultrasonic processor/display unit 28 to ascertain the condition of mounting threads 19.

Advantageously, the present thread inspection and measurement can be accomplished without removal of the tube 14 from the chassis, or the removal of the mounting flange 8 that secures the tubes to the bulk head 9. Prior art thread examination systems required the removal of the mounting flange 8 from the tube 14 which is time consuming and occasionally resulted in structural damage to the tube 14. The time and expense of tube removal from the chassis (which often required lifting cranes and cutting torches) as well as potential tube damage is minimized by practicing the present thread inspection process.

Figure 3:
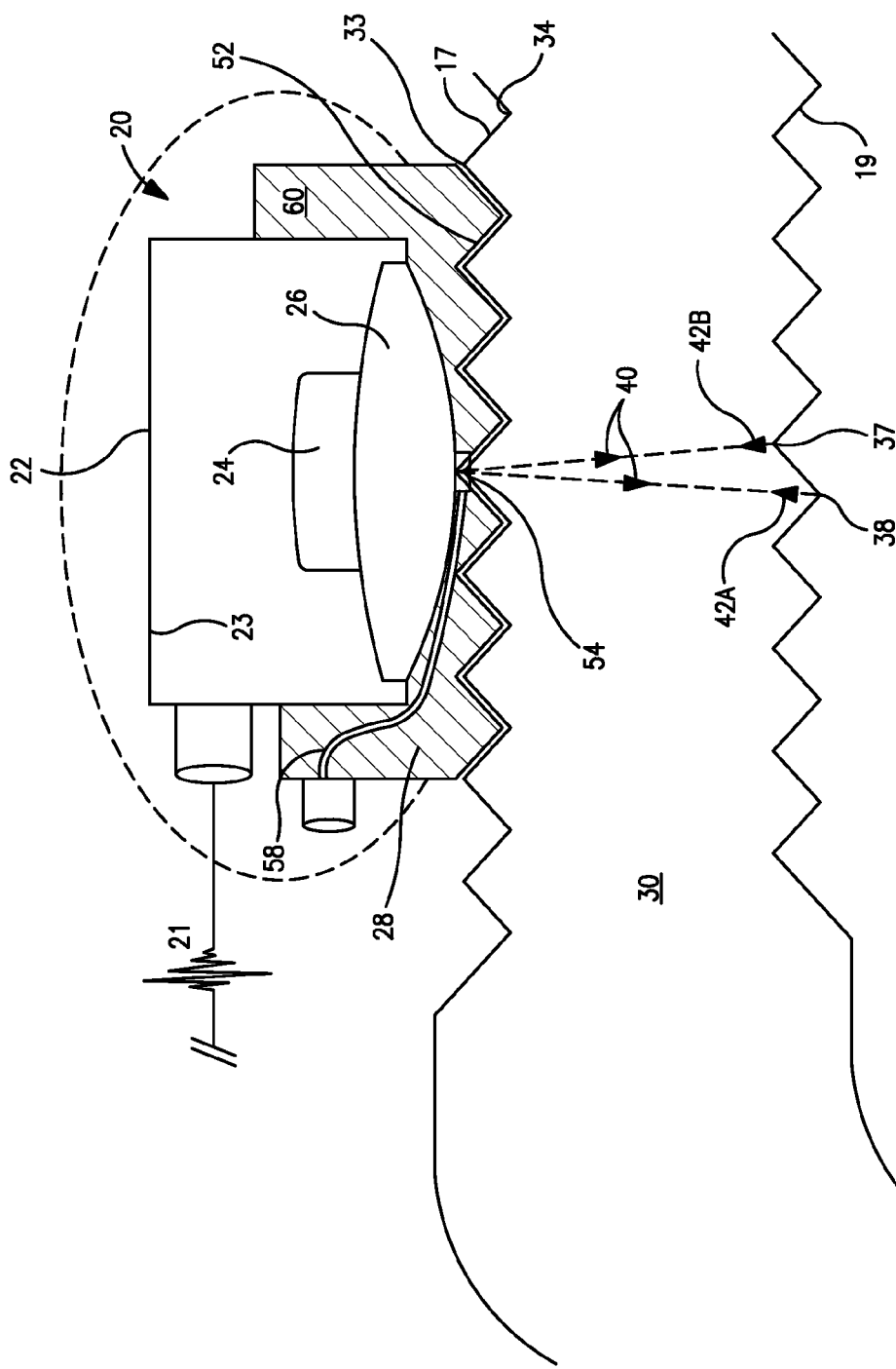
FIG. 3 is a partial cross-section illustration of the probe examining the mounting threads of a tube in accordance with the present invention.

As seen in more detail in FIG. 3, the probe 20 includes the transducer housing 23, a piezoelectric crystal 24, a contoured wear plate 26, a shoe 28, and a positioning mechanism (not shown). The probe is shown in operative association with an examination article 30 of generally solid construction that includes an ID thread 17 having an ID thread peak 33 and ID thread base 34 as well as an OD thread 19 having an OD thread base 37 and OD thread peak 38. In the disclosed embodiment, the probe 20 is placed in contact with the ID threads 17 and may be adapted to move rotationally along the ID threads 17.

The probe 20 incorporates one or more transducers for transmission and reception of ultrasound pulses at frequency ranges of about 2 MHz to about 15 MHz or more. The transducers generate ultrasonic pulses 40 at regular intervals and the ultrasonic processor/display unit 28 measures the time taken for the ultrasonic pulses 40 to pass through the examination article 30 and return to the receiver. The transducer(s) 22 is arranged so that the ultrasonic pulses 40 are focused on a single location in the examination article 30 and exit at the same location.

The ultrasonic transducer 22 includes a piezoelectric crystal 24 that converts electrical energy such as an excitation pulse into high frequency stress wave energy. The ultrasonic transducer 22 directs a high frequency stress wave energy signal from the piezoelectric crystal 24 toward the examination article 30 and receives reflected signals 42A, 42B back therefrom. The received signals are converted to electrical signals 21 which are subsequently analyzed and displayed using an ultrasonic signal processor/display unit 28 to ascertain properties of the examination article 30 such as thickness or thread condition. Using this ultrasonic measurement technique, the thickness of the examination article 30 is represented by the 'time of flight' from launch of an ultrasonic signal 40 to receipt of the reflected signal 42A, 42B provided one has knowledge of the material of the examination article 30 and the velocity through which the waves travel through the material. For threaded articles, one can also measure the time lag between the reflected signal 42A received from the base of the thread 37 and the reflected signal 42B received from the peak of the thread 38, as both the peak of the thread and the base of the thread are generally parallel to the first surface where the ultrasonic signal 40 was launched.

As is well known in the art, ultrasonic inspection requires that the probe 20 be in contact with a first surface 17 of the examination article 30 and generally aligned in a parallel orientation to the reflecting surfaces 37 and 38 of examination article 30. The probe 20 is preferably coupled to a couplant supply 59 via couplant line 58 to ensure there is sufficient coupling between the probe 20 and examination article 30.

The basic purpose of the wear plate 26 is to protect the piezoelectric crystal 24 of the ultrasonic transducer 22 from the testing environment. In the case of ultrasonic transducers, the wear plate 26 must be a durable and corrosion resistant material in order to withstand the wear caused by repeated use on materials such as steel. The contoured wear plate 26 of the present embodiment is preferably machined to the contour of the threaded first surface 17 of the examination article 30. More specifically, the wear plate 26 is preferably contoured to the radius of the ID threads 17 of the examination article 30. This contour allows optimum contact between the wear plate 26 and the peak of the thread 33 through which the ultrasonic waves will pass into the examination article 30. The contoured surface of the wear plate 26 operates to improve the signal to noise ratio and also provides the requisite alignment between the first surface (i.e. peak of the ID thread through which the ultrasonic waves will pass into the examination article) and the reflected surfaces 37 and, 38 namely the base of the OD thread and peak of the OD thread. The preferred contoured wear plate 26 is made of alumina which is extremely abrasion resistant and has an acoustic impedance value between that of the piezoelectric crystal 24 in the ultrasonic transducer 22 and the material of the examination article 30 being inspected. The opposite surface of the contoured wear plate is curved to act as a lens such that the output of the piezoelectric crystal 24 is focused into a narrow beam at window 54 where it enters the examination article 30.

The shoe 28 is a structure attached to the housing 23 and includes a thread-like exterior surface 52 disposed adjacent to the contoured wear plate 26. The thread-like exterior surface 52 of the shoe 28 is adapted to be disposed on the first surface 17 of the examination article 30, which in the disclosed embodiment is a threaded surface. The shoe 28 further includes a window 54 or port disposed at or near the apex of the contoured wear plate 26. The thread-like shape of the exterior surface 52 of the shoe 28 generally matches the threaded shape of the threaded first surface 17 on the examination article 30. The cooperative engagement of the thread-like shape of the exterior surface 52 of the shoe 28 and the threaded first surface 17 on the examination article 30 aligns, in part, the narrow window 54 with a thread peak 33 on the threaded first surface 17 and further fixes the orientation of the ultrasonic transducer(s) 22 within the probe 20 to an angle optimized for measuring the opposite threaded surface 19 of examination article 30.

The window 54 in the shoe 28 is a narrow opening or portal that allows a portion of the transmitted stress wave energy 40 generated from the ultrasonic transducer(s) 22 to pass to the examination article 30 without being absorbed. More specifically, a portion of the stress wave energy generated from the ultrasonic transducer(s) 22 passes through the contoured wear plate 26 and through the narrow window 54 into the thread peak 33 of the examination article 30 and is reflected back thru the narrow window 54 from the base and peak of the opposite threads 19 on the examination article 30.

A couplant line 58 or other supply means adapted to supply ultrasonic couplant to a location near the surface of the ultrasonic transducer(s), and more particularly to the area proximate the window 54 of the shoe 28 is also provided. The presence of the ultrasonic couplant facilitates coupling between the ultrasonic transducer(s) 22 and the threaded first surface 17 on the examination article 30. The ultrasonic couplant is preferably a viscous fluid such as oil further serves as a lubricant to protect the contour wear plate and shoe from unnecessary abrasion.

The shoe 28 further includes an absorber material 60 surrounding the area proximate the ultrasonic transducer(s) 22. The absorber material 60 preferably has matched acoustic impedance to that of the contoured wear plate 26 so as to allow efficient transmission of the ultrasonic waves from the ultrasonic transducer(s) 22 into the absorber material 60. The absorber material 60 is highly attenuative so as to absorb the energy through beam scattering and heat conversion. In doing so, the absorber suppresses most of the ultrasonic transmission from the piezoelectric crystal 24 except for the transmission through the narrow window 54. The absorber material 60 also provides efficient absorption of the signals reflected back from the examination article 30 that are not received through the narrow window 54.

In the preferred embodiment, the absorber material 60 is made of an epoxy (e.g. 3M Scotchcast Electrical Resin, Product #226 (Part A and B)) containing fine tungsten powder (e.g. Atlantic Equipment Engineers, Product Code WP-102, 99% 1-5 micrometer Tungsten Powder). The amount of tungsten powder present in the epoxy can be varied to alter the acoustic impedance so as to match or approximate the acoustic impedance of the contoured wear plate 26 and examination article 30. The mix of epoxy and tungsten powder is also highly attenuative as a result of the scatter of the ultrasonic wave at the tungsten interface and absorption by heat conversion into the epoxy. Moreover, the tungsten and epoxy material can be easily cast into a variety of complex shapes, including thread-like shapes to help align the ultrasonic transducer(s) with the threaded first surface.

Using the contoured wear plate 26 and the shoe 28, the ultrasonic waves 40 launched from the piezoelectric crystal 24 are precisely controlled so as to pass into the examination article 30 only via the narrow window 54 and only when the window 54 is oriented at a thread peak 33 of the ID threads 17 and nowhere else. Also, since the narrow window 54 is the only unobstructed transmission path between the contoured wear plate 26 and the examination article 30, only reflected signals 42 aligned with the narrow window 54 are received by the ultrasonic transducer(s) 22, which generally corresponds to the reflected signals 42A and 42B coming from the OD base thread and OD peak thread opposite the narrow window 54.

An optional element (not shown) of the disclosed ultrasonic thread inspection device is a spring or other retention means to hold the probe against the threaded first surface 17 of the examination article. Hydraulic pressure of the couplant supplied by the conduit or couplant line 58 is sufficient to force the ultrasonic transducer(s) 20 against the spring raising it enough to allow a small amount of ultrasonic couplant to flow from the conduit onto the threaded first surface 17 of the examination article 30. Otherwise, the spring or other retention means also keeps the probe 24 in relatively stationary position vis-à-vis the examination article 30 as the measurements are taken.

Another useful feature of the disclosed ultrasonic thread inspection device is a positioning mechanism (not shown) to move the probe 20 through the entire area to be examined. In one embodiment, the positioning mechanism is a mechanical device that moves the ultrasonic inspection device 20 in a rotational manner around the threaded first surface 17 of the examination article 30. Such a rotating mechanical device can also be adapted to provide electronic x-y positioning information sufficient to construct a plot of x-y coordinates versus thread condition.

From the foregoing, it should be appreciated that the present invention thus provides a system and method for ultrasonic examination of threaded surfaces, and more particularly to ultrasonic examination or inspection of mounting threads of a tube while the tube is affixed to a tube trailer. While the invention herein disclosed has been described by means of specific embodiments and processes associated therewith, numerous modifications and variations can be made thereto by those skilled in the art without departing from the scope of the invention as set forth in the claims or sacrificing all its material advantages.

What is claimed is:

1. A method for ultrasonic inspection of threads on a tube while the tube is affixed to a trailer, the method comprising the steps of:
   removing a tube valve and an end plug from an end of the tube to define an opening on the tube exposing an interior threaded surface;
   inserting a probe into the opening in contact with the exposed interior threaded surface;
   directing test signals from the ultrasonic inspection device towards an exterior threaded surface and receiving reflected signals therefrom; and
   analyzing the reflected signals to ascertain thread conditions on the exterior threaded surface.

2. The method for ultrasonic inspection of threads on a tube of claim 1 wherein the exposed interior surface is an exposed interior threaded surface and the probe has a thread-like exterior surface adapted to fit with the exposed interior threaded surface.

3. The method for ultrasonic inspection of threads on a tube of claim 2 wherein the probe further comprises a piezoelectric crystal, a wear plate disposed adjacent to the piezoelectric crystal and a shoe having the thread-like exterior surface disposed around one or more ultrasonic transducers and the wear plate, the thread-like exterior surface further defining a window; and
   wherein the step of directing test signals further comprises transmitting ultrasonic pulses from the piezoelectric crystal and absorbing most of the ultrasonic pulses with the shoe and allowing a portion of the ultrasonic pulses to pass through the window to the exterior threaded surface.

4. The method for ultrasonic inspection of threads on a tube of claim 3 further comprising the step of supplying an ultrasonic couplant to an area proximate the window to ensure the ultrasonic pulses from the probe pass through the window to the tube.

5. The method for ultrasonic inspection of threads on a tube of claim 3 further comprising the step of forcibly retaining the ultrasonic inspection device in contact with the exposed interior surface.

6. The method for ultrasonic inspection of threads on a tube of claim 3 further comprising the step of rotating the probe along the exposed interior threaded surface.

7. An ultrasonic test instrument for use with threaded examination articles, the ultrasonic test instrument comprising;
   an ultrasonic probe having one or more transducers with a piezoelectric crystal for transmission and reception of ultrasonic signals;
   a wear plate disposed adjacent to the piezoelectric crystal to protect the piezoelectric crystal; and a shoe disposed around the probe and wear plate, the shoe further having a thread-like exterior surface adapted to fit into a threaded surface of the examination article and defining a window in said thread-like exterior surface;

a means for rotating the probe along the threads of the threaded examination article;

wherein the shoe absorbs the ultrasonic signals transmitted from the piezoelectric crystal except for the ultrasonic signals passing through the narrow window.

8. The ultrasonic test instrument of claim 7 wherein the wear plate is contoured.

9. The ultrasonic test instrument of claim 8 wherein the contoured wear plate further comprises a contoured outer surface having a radius equal to a thread radius on the threaded surface of the examination article.

10. The ultrasonic test instrument of claim 8 wherein the contoured wear plate further comprises a curved inner surface and wherein the ultrasonic signals are focused in a narrow beam to a location near the window.

11. The ultrasonic test instrument of claim 7 wherein the shoe further comprises an absorption material that is highly attenuative and has an acoustic impedance that generally matches an acoustic impedance of the wear plate or the acoustic impedance of the examination article.

12. The ultrasonic test instrument of claim 11 wherein the adsorption material is a tungsten powder suspended in an epoxy matrix.

13. The ultrasonic test instrument of claim 7 further comprising a means for retaining the probe in contact with the threaded examination article.

14. The ultrasonic test instrument of claim 7 further comprising a couplant line in flow communication to an area proximate the window and wherein the couplant line is adapted to supply an ultrasonic coupling fluid to the area proximate the window.

* * * * *